(12) United States Patent
Lui

(10) Patent No.: US 7,468,039 B2
(45) Date of Patent: Dec. 23, 2008

(54) ADJUSTABLE TENSION CUFF ASSEMBLY

(75) Inventor: Chun Kee Lui, Monroeville, PA (US)

(73) Assignee: Cook Vascular Incorporated, Leechburg, PA (US)

( * ) Notice: Subject to any disclaimer, the term of this patent is extended or adjusted under 35 U.S.C. 154(b) by 18 days.

(21) Appl. No.: 11/807,029

(22) Filed: May 25, 2007

(65) Prior Publication Data
US 2007/0282209 A1    Dec. 6, 2007

Related U.S. Application Data

(60) Provisional application No. 60/810,669, filed on Jun. 2, 2006.

(51) Int. Cl.
*A61B 5/04*    (2006.01)

(52) U.S. Cl. ............. 600/504; 128/100.1; 292/318

(58) Field of Classification Search ............. 600/480, 600/485, 499, 508, 510–511; 602/75–78; 607/118–133; 128/100.1, 101.1, 102.1, 103.1, 128/104.1, 105.1; 606/201–203; 292/318
See application file for complete search history.

(56) References Cited

U.S. PATENT DOCUMENTS

| | | | | |
|---|---|---|---|---|
| 4,190,057 A | * | 2/1980 | Hill et al. ............. | 600/488 |
| 4,256,094 A | * | 3/1981 | Kapp et al. ............. | 601/152 |
| 4,602,624 A | | 7/1986 | Naples et al. ............. | 128/784 |
| 4,628,942 A | | 12/1986 | Sweeney et al. ............. | 128/784 |
| 4,649,936 A | | 3/1987 | Ungar et al. ............. | 128/784 |
| 4,875,647 A | * | 10/1989 | Takagi et al. ............. | 248/74.3 |
| 4,926,875 A | * | 5/1990 | Rabinovitz et al. ............. | 600/504 |
| 5,092,332 A | | 3/1992 | Lee et al. ............. | 128/642 |
| 5,205,292 A | | 4/1993 | Czar et al. ............. | 128/662.03 |
| 5,289,821 A | | 3/1994 | Swartz ............. | 128/661.09 |
| 5,564,434 A | | 10/1996 | Halperin et al. ............. | 128/748 |
| 5,588,436 A | | 12/1996 | Narayanan et al. ............. | 128/662.03 |
| 5,807,258 A | | 9/1998 | Cimochowski et al. ............. | 600/454 |
| 5,941,894 A | * | 8/1999 | Hill ............. | 606/194 |
| 5,967,989 A | | 10/1999 | Cimochowski et al. ............. | 600/459 |
| 6,076,234 A | * | 6/2000 | Khokhar et al. ............. | 24/16 PB |
| 6,077,227 A | | 6/2000 | Miesel et al. ............. | 600/486 |
| 6,106,477 A | | 8/2000 | Miesel et al. ............. | 600/486 |

(Continued)

*Primary Examiner*—Charles A Marmor, II
*Assistant Examiner*—Anita Saidi
(74) *Attorney, Agent, or Firm*—Brinks Hofer Gilson & Lione

(57) ABSTRACT

A cuff assembly for placement around a body vessel comprises a cuff member sized to substantially surround the body vessel, and a tether assembly engaged with the cuff member. The tether assembly is sized to at least substantially encircle the cuff member, and includes a locking mechanism for releasably maintaining a selected tension when the tether assembly encircles the cuff member. The tether assembly may comprise a tether and a tab, wherein the tab is engaged with the cuff member and has an aperture therethrough. The distal end of the tether is engaged with the tab. The locking mechanism may comprise a plurality of stop members disposed along a surface of the tether. The stop members are sized relative to the aperture to enable passage of at least a portion of the tether therethrough to encircle the cuff member when the stop members are aligned at a first angle relative to the aperture, and to substantially fix a position of the tether at a tension around the cuff member when the stop members are aligned at a second angle relative to the aperture.

19 Claims, 10 Drawing Sheets

U.S. PATENT DOCUMENTS

| | | |
|---|---|---|
| 6,398,734 B1 | 6/2002 | Cimochowski et al. ..... 600/454 |
| 6,626,839 B2 | 9/2003 | Doten et al. ................ 600/484 |
| 6,974,416 B2 | 12/2005 | Booker et al. ............... 600/459 |

* cited by examiner

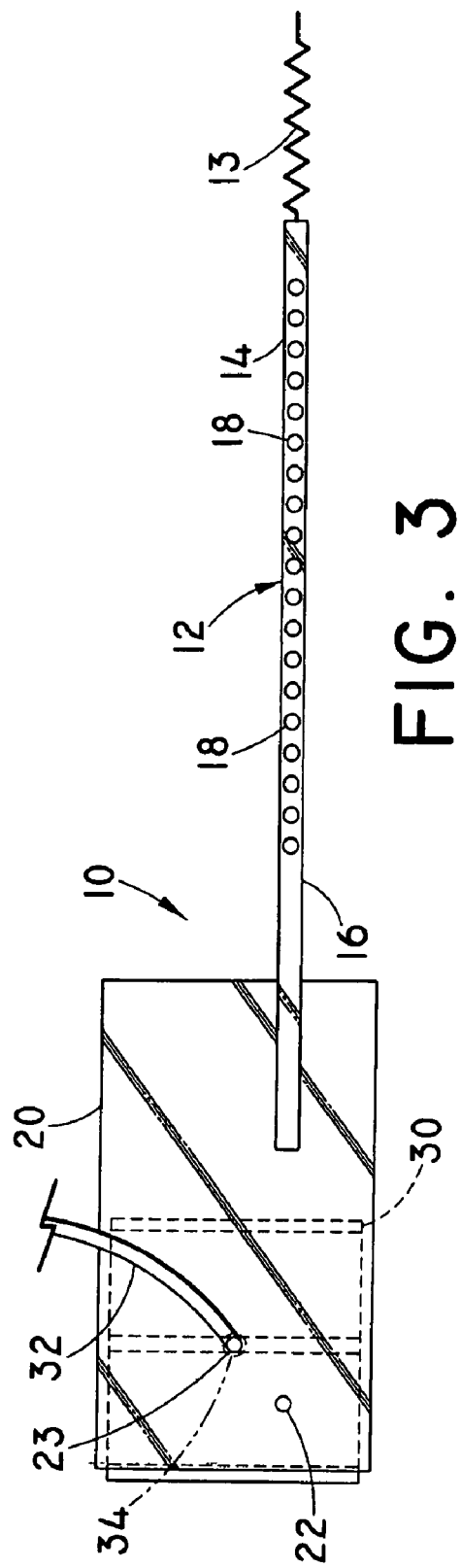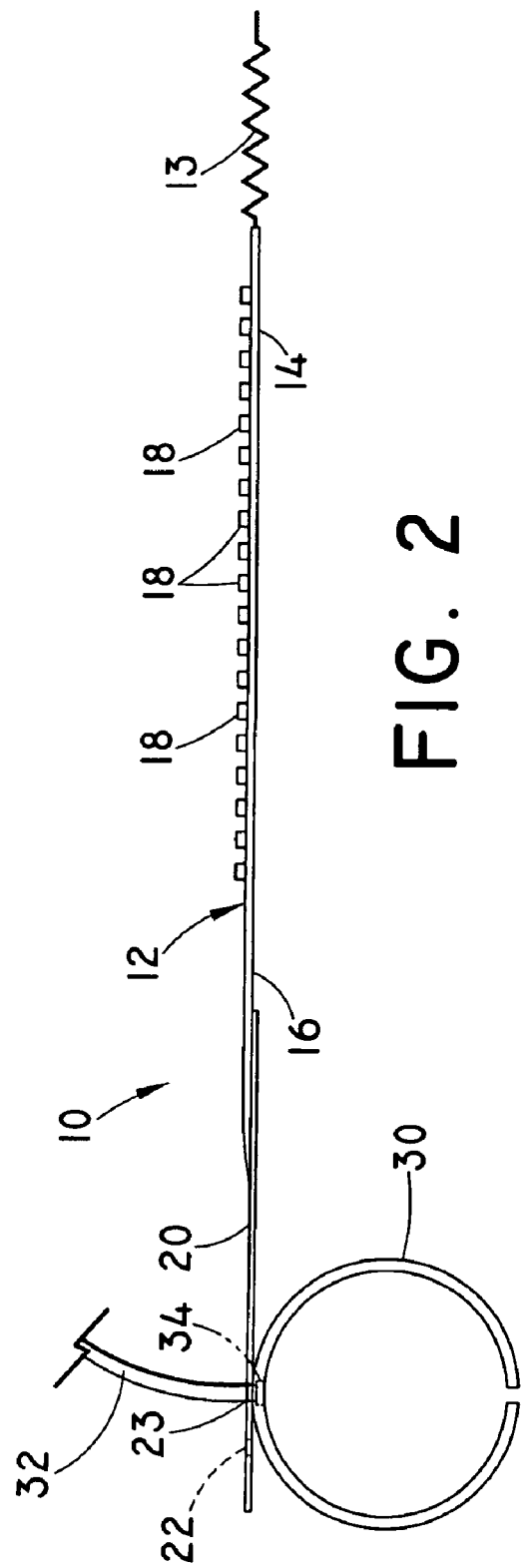

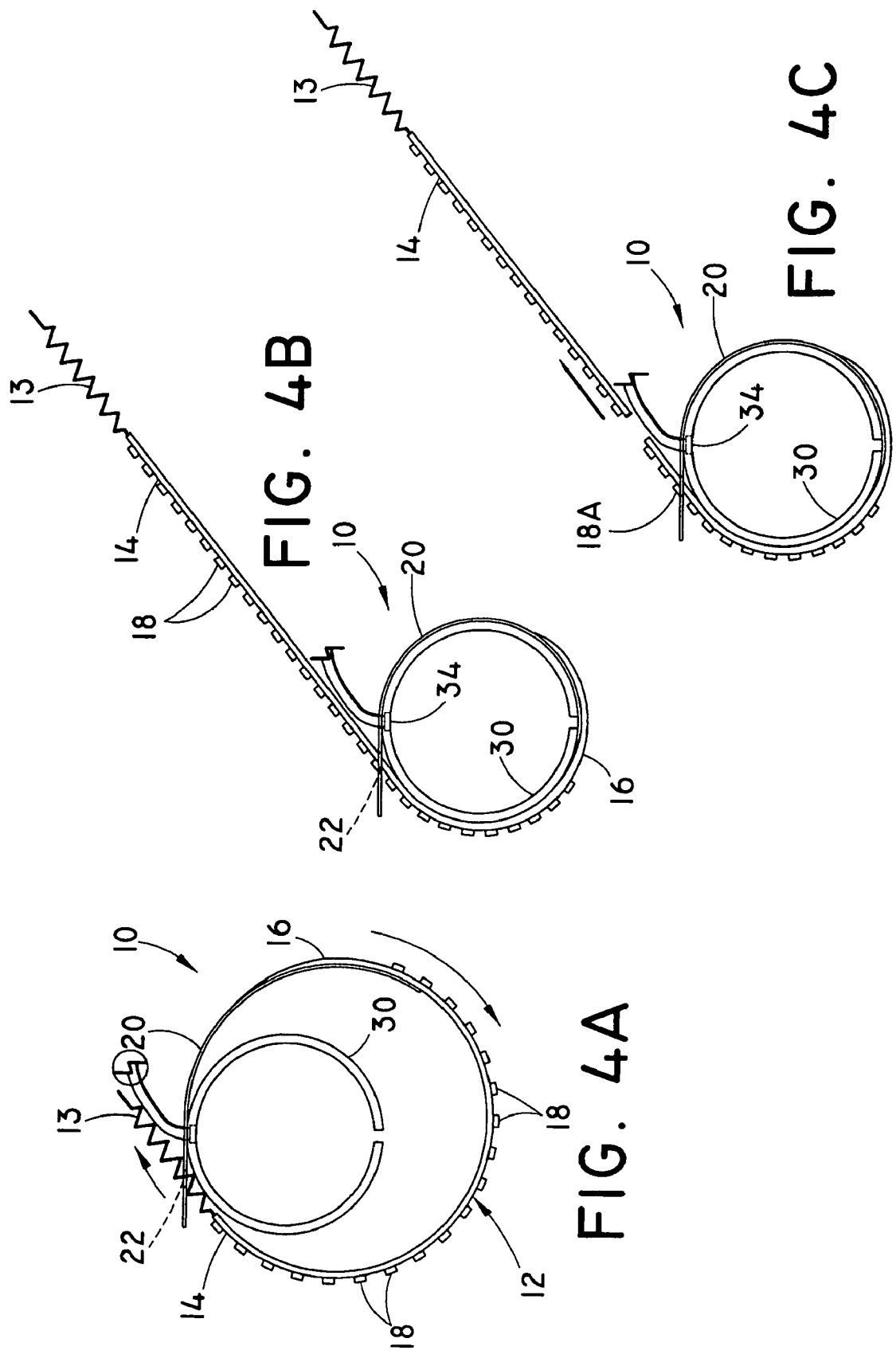

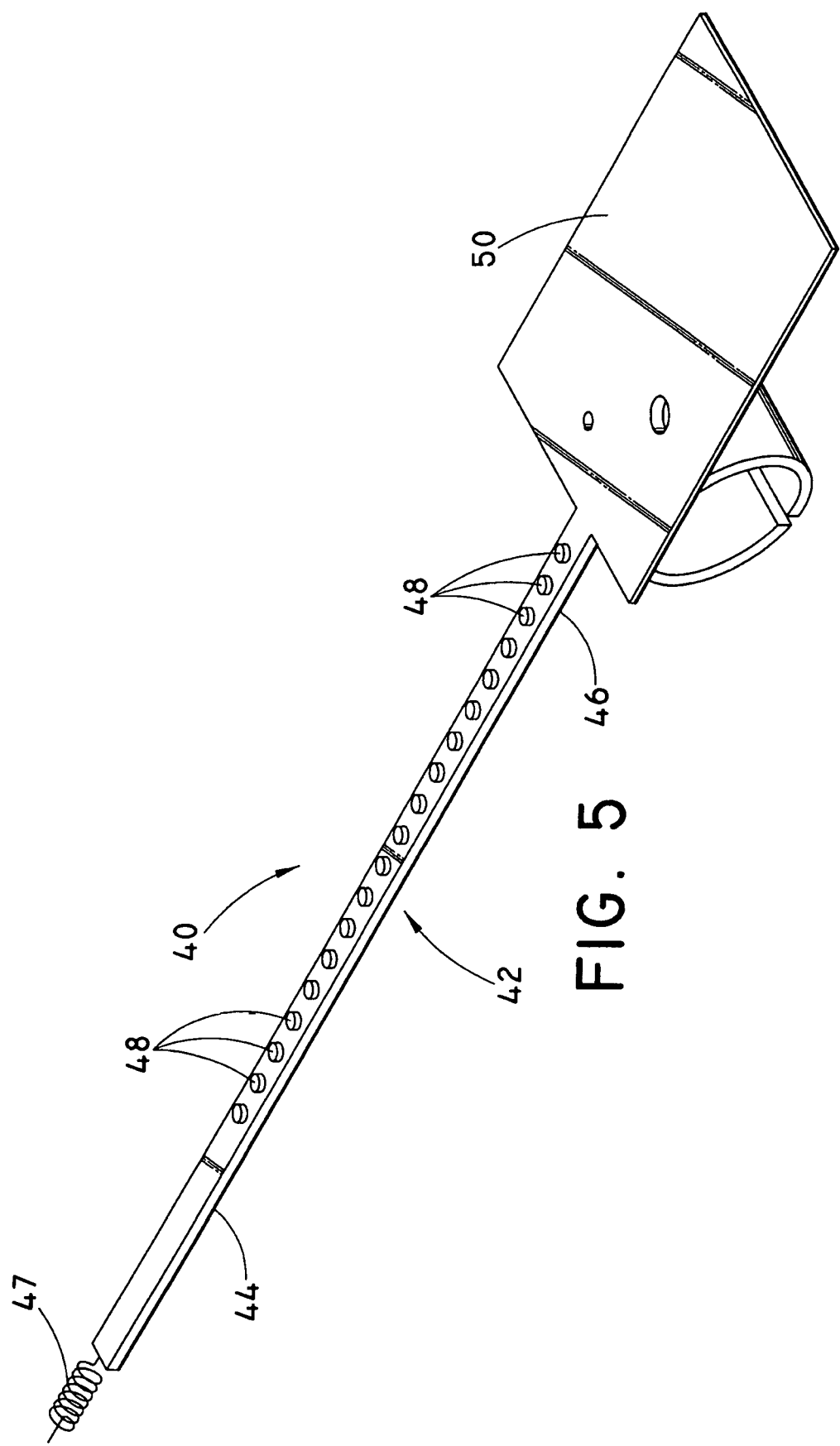

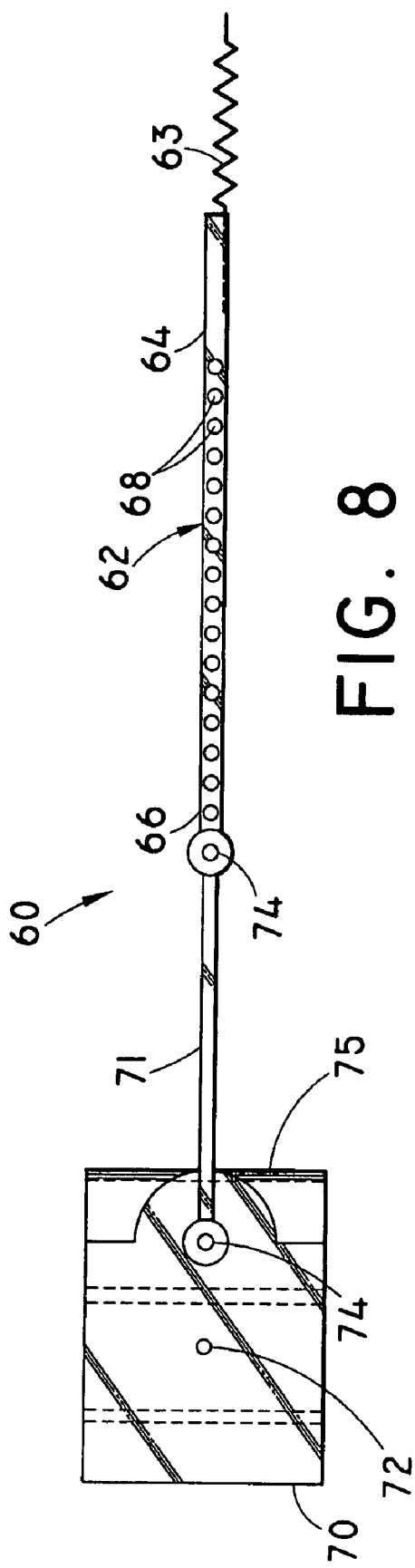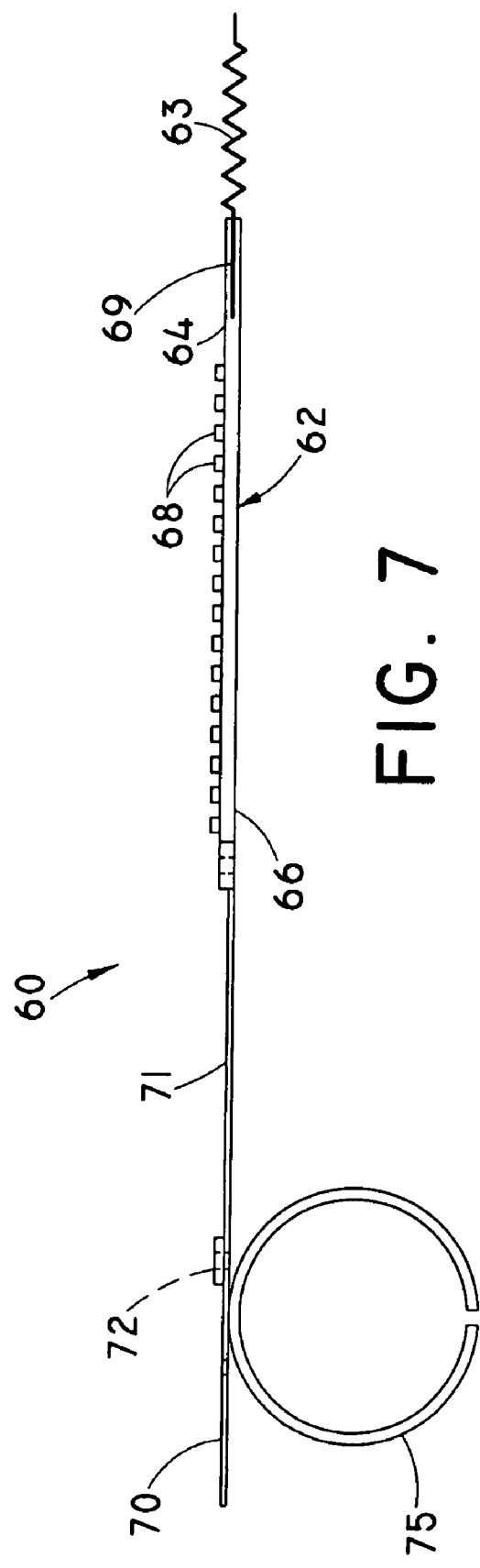

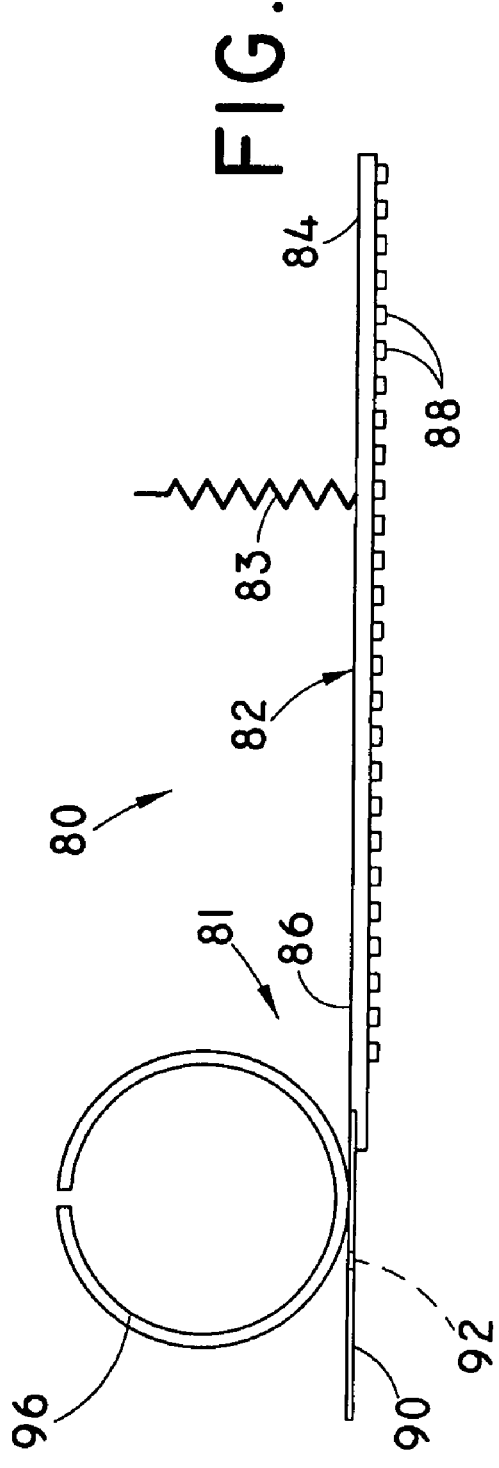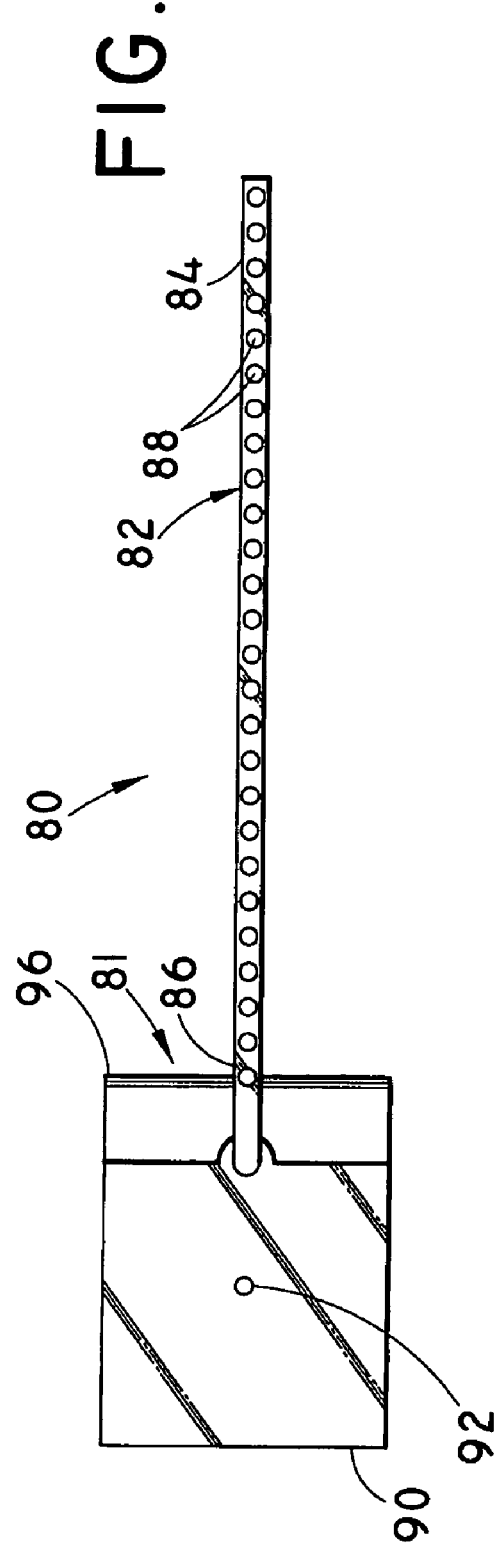

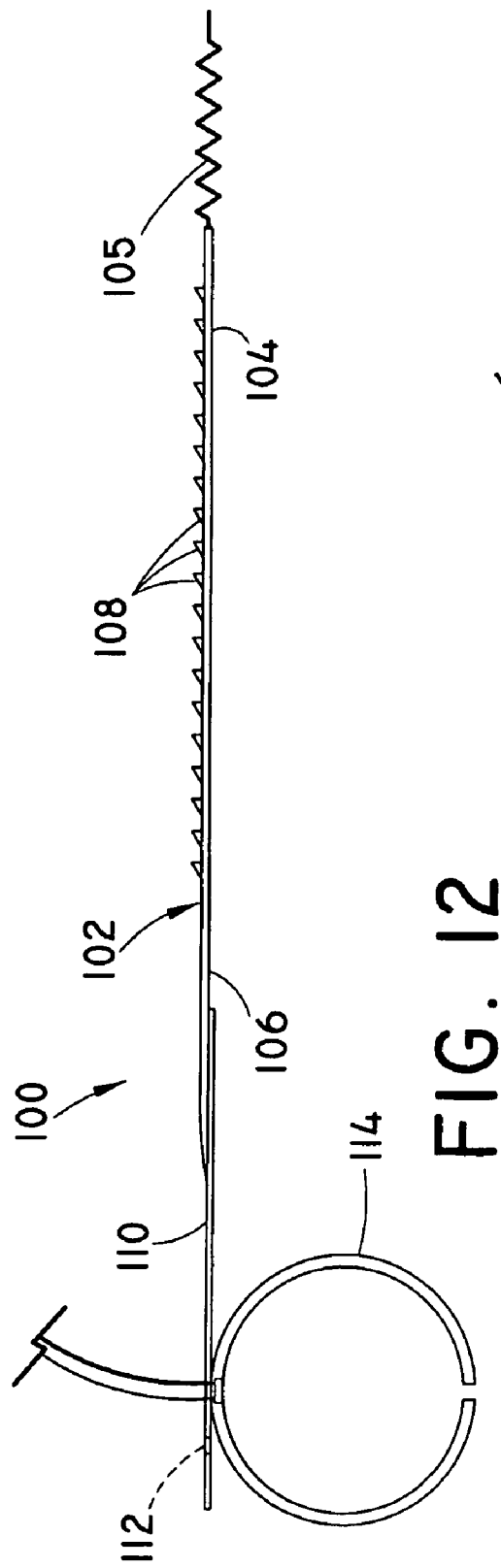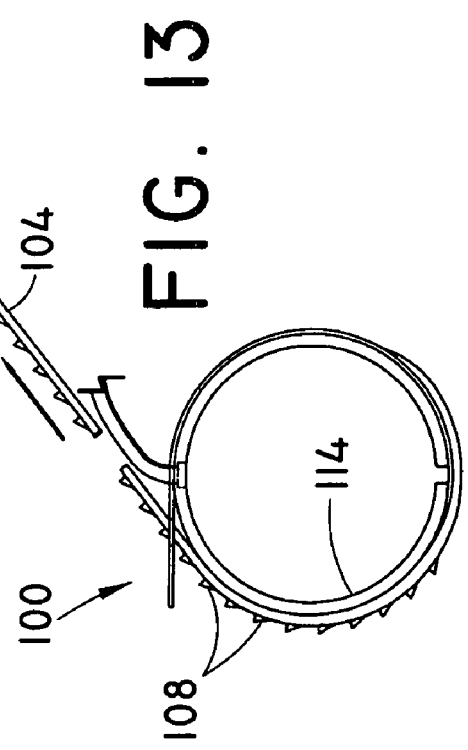

ADJUSTABLE TENSION CUFF ASSEMBLY

RELATED APPLICATION

The present patent document claims the benefit of the filing date under 35 U.S.C. §119(e) of Provisional U.S. Patent Application Ser. No. 60/810,669, filed Jun. 2, 2006, which is hereby incorporated by reference.

BACKGROUND

1. Technical Field

The present invention relates to an adjustable tension cuff assembly for use with a medical device, such as a device for monitoring the flow of a bodily fluid through a body vessel.

2. Background Information

A variety of microsurgical procedures have been developed in recent years which have saved the lives of patients, and/or significantly improved the quality of life for patients. Such procedures include organ transfer surgery, reconstructive surgery following the removal of tumors (particularly in the areas of the head and neck), coronary artery bypass grafting (CABG) procedures, and reconstructive surgery such as free tissue transfer and the like. Free tissue transfer typically entails the removal of tissue and/or muscle from one part of the body, along with an associated artery and vein, and the reattachment of the tissue and/or muscle to another part of the body. The artery and vein of the transferred tissue and/or muscle are then anastomosed (that is, connected) to a native artery and vein in order to achieve blood circulation in the transferred tissue and/or muscle.

The success of such transfer or reconstruction lies in obtaining good patency of the anastomosis, and hence, good patency in the transferred tissue and/or muscle (sometimes referred to as the flap). A primary complication in microvascular surgery such as free tissue transfer is thrombosis. Unrecognized thrombosis reduces patency in the flap and reduces the probability of salvaging the flap. The window of opportunity for salvage after thrombosis is presently believed to be only about six hours of warm ischemia. It is therefore critical that any vascular thrombosis in a transferred flap be recognized and any resulting ischemia be remedied as soon as possible. While the success rate of the free tissue transfer procedure is generally quite favorable, it is desired to improve the success rate to an even greater degree. Even though failure rates are generally low, any surgical failure can be costly, both to the patient and the medical provider. It would be highly desirable to reduce the failure rate of this and similar techniques.

A variety of operative and post-operative monitoring techniques are presently used for clinically assessing thrombosis and identifying the resulting ischemia. One widely-used technique utilizes an implantable ultrasonic Doppler probe that is positioned directly on the anastomosed vein and/or the artery. Such a probe includes an implanted piezoelectric transducer carried on a cuff or sleeve that is wrapped around the blood vessel of interest. The transducer is used to alternately generate ultrasonic waves and measure backscattering of those waves. Since blood is a very effective backscattering medium, the Doppler shift in the frequency of the backscattered ultrasonic waves yields a precise and accurate measurement of the blood velocity and, by implication from the cross-sectioned area of the blood vessel, the volume of blood flow in the vessel of interest. Monitoring of blood flow in this manner normally provides effective early warning of thrombosis, thereby significantly increasing the chances of salvaging the flap.

In this technique, the cuff is snugly arranged around the vessel, and the respective ends of the cuff are joined by sutures or by a clip. This manner of attachment has certain drawbacks. For example, if an inadequate signal is attained, it is often necessary to remove the clip or sutures, and reposition the cuff and transducer in a manner such that a stronger signal is received. In this event, the clip or sutures must be removed, the cuff must be rearranged, and the clip or sutures must then be reattached at the new position. In addition, there are numerous possible vessels in the body of the patient that may be subject to monitoring for fluid flow. Although it would be desirable to have a separate cuff available to fit each size vessel, this is often not possible in actual practice. As a result, for example, it may be necessary to wrap a large cuff around a small vessel. In this event, the large diameter of the cuff may make it cumbersome to work with, and may obstruct at least a portion of the signal from the transducer.

Another drawback to the use of the conventional cuffing arrangement occurs when such cuffs are used with pediatric patients. With pediatric patients, the vessel of interest may continue to grow subsequent to installation of the cuff. In this event, a cuff whose ends are secured by a clip or by sutures may undesirably restrain the vessel from expanding. While a cuff may be secured using a clip or sutures fabricated from bio-absorbable/dissolvable material, the cuff may later migrate and erode through the patient's skin. Yet another drawback with such conventional cuffs is that the tension of the cuff on the patient's vessel may not be known until the cuff has been secured on the vessel. If it is determined that the cuff is too tight, or too loose, then the clip or sutures must be removed, and the cuff must generally be replaced with a new cuff.

Other known devices and techniques have their own drawbacks. Accordingly, it would be highly desirable to provide a cuff assembly for use in a medical device, such as a device for monitoring fluid flow through a vessel during or after a surgical procedure, wherein the cuff assembly can be easily and quickly attached to a body vessel, and can be easily and quickly removed, realigned and/or reattached if necessary. It would also be highly desirable to make such an assembly suitable for use with vessels of varying sizes. In addition, it would be highly desirable that the assembly be susceptible of re-adjustment if it is determined that the initial placement attained when the assembly is wrapped around the vessel is inadequate, or when a suitable initial placement or tension later becomes unsuitable due to a change in conditions, such as the growth of the vessel.

BRIEF SUMMARY

The present invention addresses the problems existing in the art. In one form thereof, the invention comprises a cuff assembly for placement around a body vessel. The cuff assembly comprises a cuff member sized to substantially surround the body vessel, and a tether assembly engaged with the cuff member. The tether assembly is sized to at least substantially encircle the cuff member, and includes a locking mechanism for releasably maintaining a selected tension when the tether assembly encircles the cuff member. The tether assembly may comprise a tether and a tab, wherein the tab is engaged with the cuff member and has an aperture therethrough. The distal end of the tether is engaged with the tab. The locking mechanism may comprise a plurality of stop members disposed along a surface of the tether. The stop members are sized relative to the aperture to enable passage of at least a portion of the tether therethrough to encircle the cuff member when the stop members are aligned at a first angle relative to the aperture, and to substantially fix a position of the tether at a tension around the cuff member when the stop members are aligned at a second angle relative to the aperture.

In another form thereof, the invention comprises a method for monitoring fluid flow in a body vessel. A cuff assembly comprises a cuff member sized to at least substantially encircle the body vessel, and a probe member operationally engaged with the cuff member to provide a signal corresponding to fluid flow in the vessel. A tether assembly is engaged with the cuff member and sized for at least substantially surrounding the cuff member. The tether assembly has an aperture therein and a plurality of stop members disposed along a surface thereof and receivable through the aperture to a selected length for maintaining a selected tension when the tether assembly at least substantially surrounds the cuff member. The cuff assembly is positioned such that the cuff member substantially encircles the body vessel, and the probe member is aligned for providing the signal. A length of the tether assembly is wrapped around at least a portion of the cuff member, and a portion of the wrapped tether assembly, including at least one or more of the stop members, is threaded through the aperture to the selected length. The position of the stop members may then be adjusted relative to the aperture to substantially hinder withdrawal of threaded stop members back through the aperture.

In yet another form thereof, the invention comprises an adjustable tension cuff assembly for positioning around a body vessel. The assembly comprises a cuff member sized to at least substantially encircle the body vessel, a tab member engaged with a surface of the cuff member and having an aperture therethrough, and a generally flexible tether engaged with the tab member and having a length sufficient to substantially surround the cuff member when the cuff member at least substantially encircles the body vessel. A surface of the tether has a plurality of stop members disposed along at least a portion thereof. The stop members are sized and configured relative to the aperture to selectively enable passage of the tether and stop members through the aperture to at least substantially surround the cuff member and substantially fix a position of the tether at a tension around the cuff member, and to selectively enable withdrawal of the stop members through the aperture to remove the tension.

BRIEF DESCRIPTION OF THE DRAWINGS

FIG. 2 is a side view of the adjustable tension cuff assembly of FIG. 1;

FIG. 3 is a top view of the adjustable tension cuff assembly of FIG. 1;

FIGS. 4A, 4B and 4C are side views of the cuff assembly shown in FIG. 1 shown in various stages as the cuff assembly is wrapped around a blood vessel;

FIG. 5 is a perspective view of an alternative embodiment of an adjustable cuff assembly;

FIG. 7 is a side view of the adjustable tension cuff assembly of FIG. 6;

FIG. 8 is a top view of the adjustable tension cuff assembly of FIG. 6;

FIGS. 9-11 illustrate another alternative embodiment of the inventive adjustable cuff assembly;

FIGS. 12 and 13 illustrate still another alternative embodiment of the inventive adjustable cuff assembly;

DETAILED DESCRIPTION OF THE DRAWINGS AND THE PRESENTLY PREFERRED EMBODIMENTS

Figure 1:
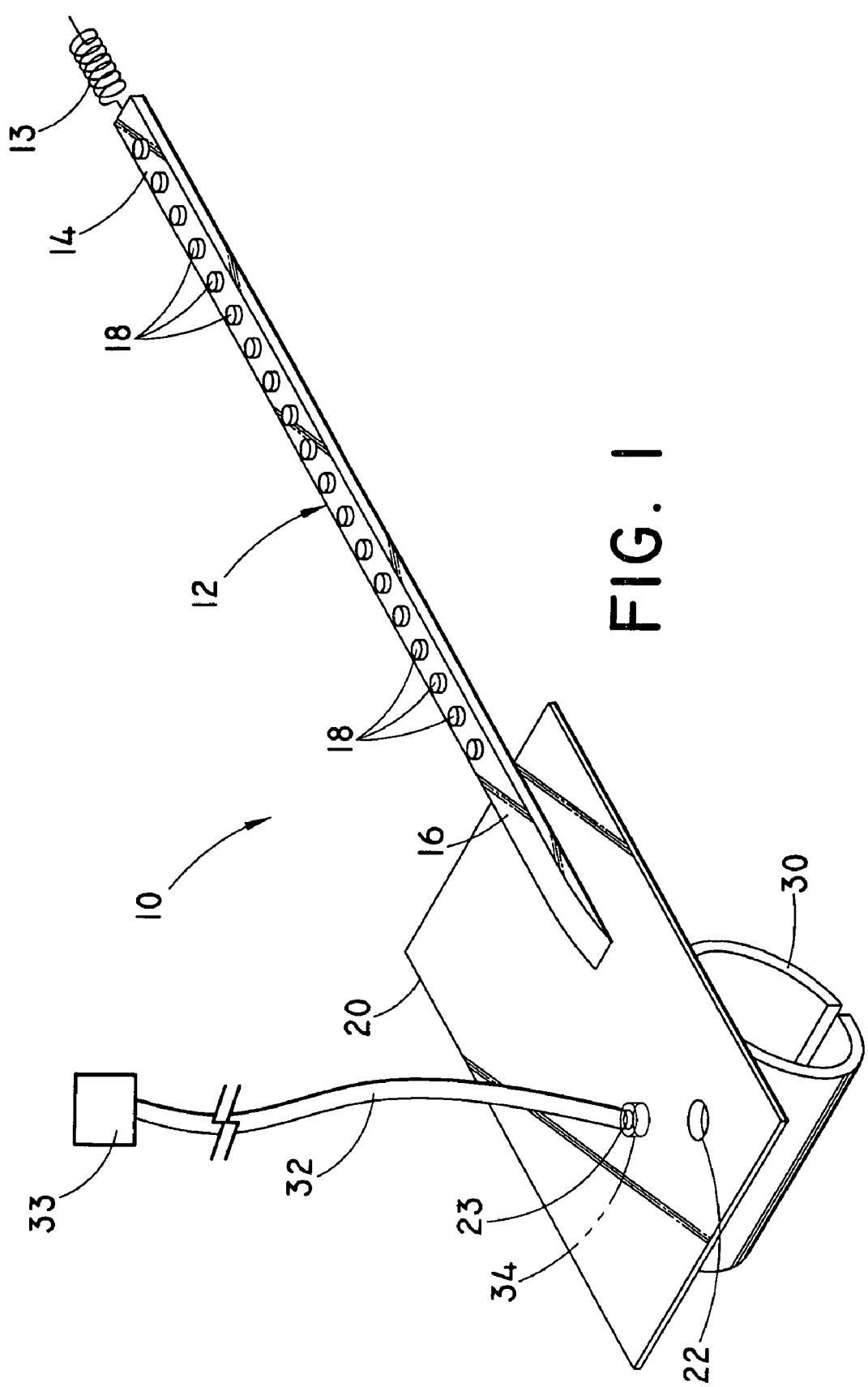
FIG. 1 is a perspective view of an adjustable cuff assembly according to an embodiment of the present invention.

For purposes of promoting an understanding of the present invention, reference will now be made to the embodiments illustrated in the drawings, and specific language will be used to describe the same. It is nevertheless to be understood that no limitation of the scope of the invention is thereby intended. The figures are not all drawn to the same scale to avoid obscuring the details of the finer structures. The following detailed description of the preferred embodiments will make clear the preferred arrangement, size relationships and manner of using the components shown herein.

The present invention relates to an adjustable tension cuff assembly of the type that may be placed around a body vessel of a patient. Such a cuff may be used, for example, in connection with a piezoelectric transducer for measuring fluid flow through a blood vessel. In the following discussion, the terms "proximal" and "distal" will be used to describe the opposing axial ends of the assembly, as well as the axial ends of various component features of the assembly. The term "proximal" is used in its conventional sense to refer to the end of the assembly (or component) that is closest to the operator during use of the assembly. The term "distal" is used in its conventional sense to refer to the end of the assembly (or component) that is initially inserted into the patient, or that is in closest proximity to the patient.

Doppler probe devices for monitoring fluid flow in a body vessel are well known in the medical arts. In prior art devices, a piezoelectric transducer is typically secured to or within a flexible cuff that is sized to be wrapped around the vessel of interest, such as a blood vessel. The transducer is oriented along the vessel in a manner such that it receives a signal from the vessel that corresponds to a flow of fluid in the vessel. One or more insulated wires extend from the transducer to a processing unit. The processing unit receives the signal from the transducer via the insulated wires, and translates the signal to a data readout that provides a graphic measurement of fluid flow in the vessel. Prior art assemblies of this type are described, among others, in U.S. Pat. Nos. 5,289,821 and 5,588,436, incorporated by reference herein.

In prior art devices, the cuff is typically wrapped around the vessel, and the respective ends of the cuff are joined by means such as a clip or by sutures. As stated previously, this manner of attachment is subject to certain shortcomings, which shortcomings become particularly apparent if it is necessary to remove or reposition the cuff. If such removal or repositioning is required, the clip or sutures must be removed. If desired, the cuff may then be adjusted, and the respective ends of the cuff must be rejoined by once again clipping or suturing the ends.

The adjustable tension cuff assembly of the present invention enables the physician to remove, or reposition, a cuff around a blood vessel in a very simple and convenient manner that does not require complicated manipulations such as the removal and/or repositioning of clips or sutures. FIGS. 1-3 illustrate one embodiment of an adjustable tension cuff assembly 10 according to the present invention. Assembly 10 includes a generally flexible tether 12 having a proximal end 14 and a distal end 16. Tether 12 has a plurality of extensions, such as bumps 18, extending transversely along a surface, such as the upper surface, of the tether. Distal end 16 of tether 12 is affixed to a tab 20 having an aperture 22 therethrough. Tab 20 and tether distal end 16 may be affixed by any convenient, but secure, means, such as adhesion. Aperture 22 is sized to allow tether 12 and bumps 18 to pass therethrough during positioning of the cuff. Although the aperture is illustrated in the figures and described herein as a discrete ring bordered on all sides by the tab, this is shown merely for convenience, and not by way of limitation. The aperture can alternatively comprise other configurations suitable for the purposes described. One non-limiting example is an open-ended slot into which the tether and bumps can be inserted from a side of the tab.

In the embodiment shown, a non-linear lead-in portion 13 is provided that extends from the proximal end of the tether. Lead-in portion 13 facilitates capture of the tether by the aperture 22 upon initial entry of tether proximal portion 14 into the aperture, and in particular, assures that the tether does not retreat during initial placement when the physician releases his grip on the tether. Preferably, lead-in portion 13 comprises a coil as shown in the figures, although other configurations that serve the intended purpose may be substituted. The coil can extend from the proximal end of the tether as shown, or alternatively, the coiled portion can extend into a barrel portion of the proximal end of the tether.

A cuff 30 is attached to the underside of tab 20. Cuff 30 comprises a strip of flexible material that is sized and shaped to be wrapped around the vessel of interest. A piezoelectric transducer 34 (shown in phantom in the figures) is affixed on or within the cuff in a conventional fashion known in the art. A plurality of wires 32 may extend from the transducer, e.g. through a second aperture 23 in the tab, to a processing unit 33 (shown schematically) suitable for reading the signal from the transducer and translating the signal into a suitable form for readout. In the embodiment shown, the wires are shown encased within a single insulating medium. This is exemplary only, and each wire can be separately insulated if desired.

FIGS. 4A, 4B and 4C illustrate the manner in which cuff assembly 10 is manipulated as it is secured around a body vessel, such as a blood vessel (not shown). Initially, tether 12 is wrapped around the cuff by winding lead-in portion 13 and proximal end 14 around the cuff in the direction of the arrow shown in FIG. 4A. Proximal end 14 is then threaded through aperture 22 in the direction shown. After proximal end 14 passes through aperture 22, the tether is advanced in the direction shown by the arrow in FIG. 4B until the tether and tab substantially encircle the cuff 30. The tether is then further advanced to a desired tightness around the cuff. At this tightness, the cuff is compressed around the vessel in a manner such that transducer 34 is positioned to receive a signal from the vessel corresponding to a fluid flow in the vessel. After the last bump 18A (FIG. 4C) passes through aperture 22 for cuffing a particular vessel, tether 12 and tab 20 are angled relative to one another in a manner such that bump 18A as well as the other bumps that have passed through the aperture are prevented from retreating in a backward direction through aperture 22. As a result, the tether is essentially locked into the position shown in FIG. 4C.

If the physician determines that the amount of tension in the cuff is insufficient to maintain proper positioning of the cuff on the vessel, or alternatively, is excessive to an extent such that it can cause discomfort to the patient and/or damage to the vessel, the tether and tab can be manipulated to adjust the level of tension. If it is desired to increase the tension, the tether can be manipulated such that additional bumps can be threaded through the aperture in the manner shown in FIGS. 4A and 4B. If it is desired to reduce the tension, one or more bumps can be withdrawn through the aperture in the direction opposite the arrows in FIGS. 4A and 4B. Similarly, if the physician determines that the initial positioning of the cuff on the vessel provides an insufficient signal to the processing unit, the tension on the cuff may be relaxed, and the cuff may be repositioned to another portion of the vessel at which a better signal may be transmitted. In this event, the physician can simply loosen the cuff by withdrawing bumps back through the aperture in the manner described, reposition the cuff as desired, and re-establish tension in the cuff by threading bumps through the aperture in the direction of the arrows. Thus, upon either occurrence, the adjustable tension mechanism of the inventive assembly enables the physician to readily alter the tension and/or position of the cuff as desired. Following confirmation of a desired tension and/or cuff placement, the excess proximal portion of tether 12 and lead-in portion 13 may be simply snipped off and removed, as shown in FIG. 4C.

FIG. 5 illustrates a perspective view of an alternative embodiment of an adjustable tension cuff assembly 40. Cuff assembly 40 is generally similar to assembly 10, and includes tether 42, having a proximal end 44 and a distal end 46. A proximal lead-in portion 47 may be provided if desired. A plurality of transversely extending bumps 48 is positioned along a surface of tether. In this embodiment, bumps 48 extend substantially to tab 50. Tab 50 may be formed to be integral with tether 42, or otherwise affixed to it in any conventional fashion. If the cuff is to be placed around a very small vessel, it may be necessary to extend bumps 48 closer to tab 50 than in the previous embodiment. Similarly, it may not be necessary to extend bumps 48 substantially to the proximal end as in the previous embodiment. As yet another alternative, in order to provide an even more versatile assembly, bumps can be arranged along substantially the entire length of the tether, or alternatively, in discrete groupings, or segments, of bumps along the length of the tether.

Figure 6:
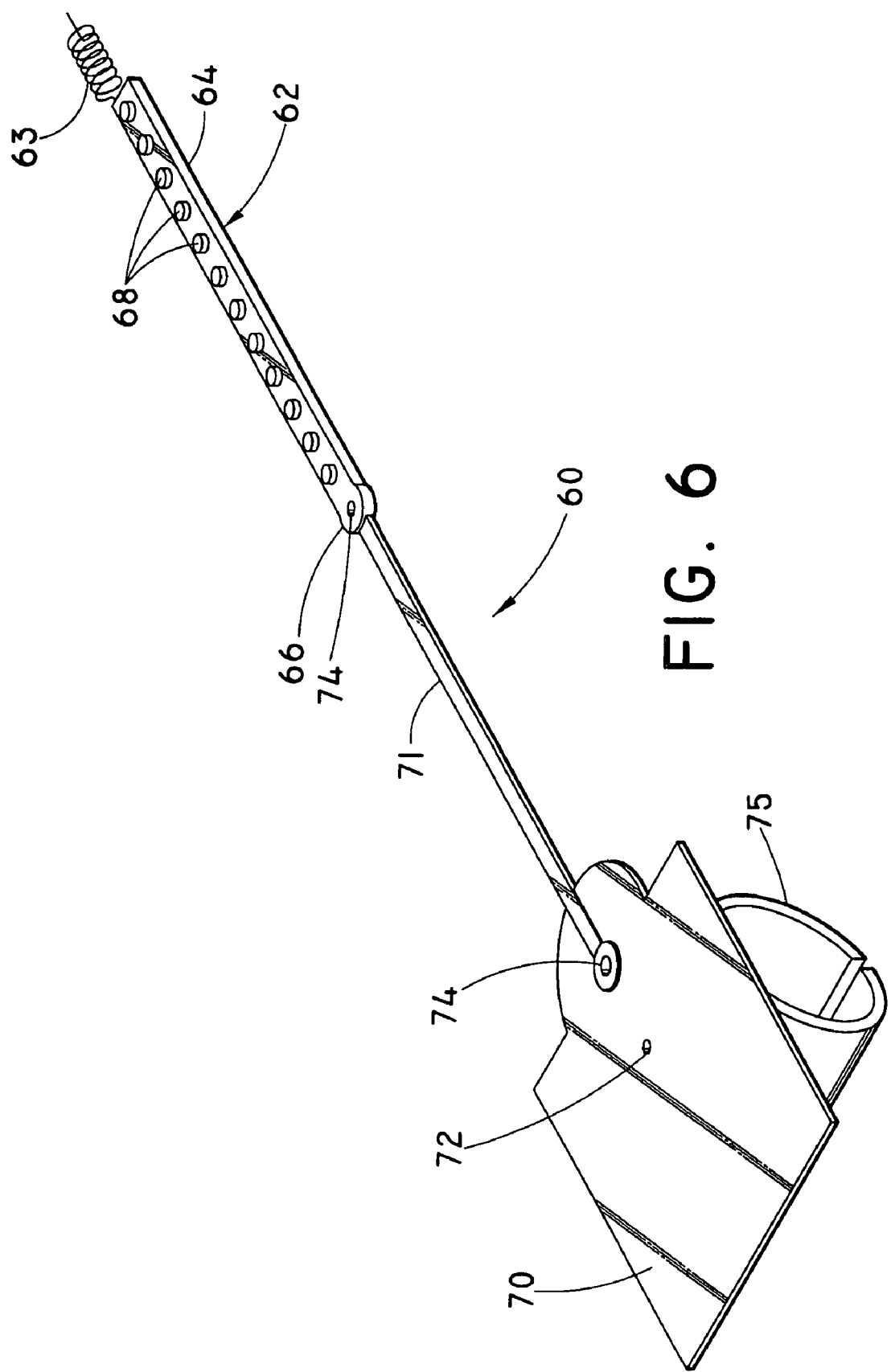
FIG. 6 is a perspective view of yet another alternative embodiment of an adjustable cuff assembly.

FIGS. 6-8 illustrate another embodiment of the inventive adjustable tension cuff assembly 60. Assembly 60 includes a generally flexible tether 62 having a proximal end 64 and a distal end 66. A plurality of bumps 68 extend transversely along an upper surface of the tether. In this embodiment, an extension 71 extends between tether 62 and a tab 70. Once again, tab 70 includes an aperture 72 for receiving tether 62. A non-linear lead-in portion 63 may be provided at the proximal end of tether 62. In this embodiment, a leading end of lead-in portion 63 is received in a chamber 69 formed along the proximal end of tether 62.

In order to minimize the amount of material left in the body following application of the apparatus, extension 71 may be dimensioned to have a smaller width and/or diameter than tether 62. Extension 71 is provided to maintain the cuff 75 around the body vessel to prevent migration of the cuff. When the tether is wrapped around the vessel, and the leading end of the tether is advanced through aperture 72 as shown in FIGS. 4A-4C, slack will be generated by the extra length of extension 71. Preferably, this slack may be taken up by a dissolvable suture. Prior to attaching the cuff 75 to the blood vessel, the physician threads the dissolvable suture through each of the through-holes 74, and ties the ends together with a knot to pull the two through-holes together. This causes extension 71 to collapse to a loop, which loop will later provide slack when the suture dissolves. This slack will eliminate the stress that would otherwise be exerted on, e.g., a growing pediatric blood vessel. As an alternative to the threading of the dissolvable suture by the physician as described, the manufacturer of the apparatus may tie the dissolvable suture (or install a dissolvable clip or other appropriate structure) during manufacture of the apparatus. However, as well known to those skilled in the art, the sterilization of dissolvable sutures, etc., can be problematic, and must be undertaken with a great deal of care. In addition, dissolvable sutures, etc., typically require special packaging. Thus, it is believed to be advantageous to have the physician tie the dissolvable sutures during installation of the apparatus.

Figure 11:
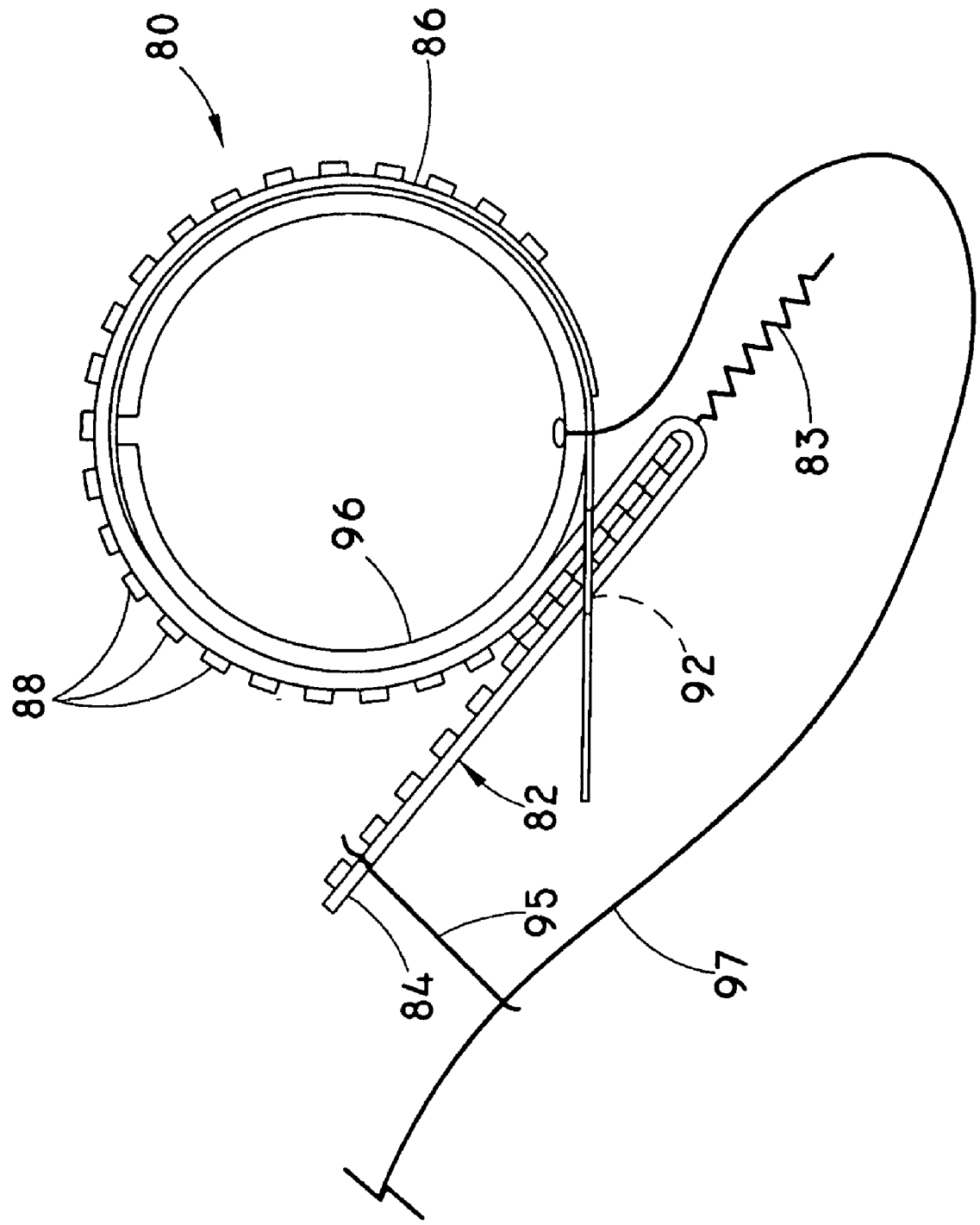

Yet another embodiment of an adjustable tension cuff assembly is shown in FIGS. 9-11. Assembly 80 includes a generally flexible tether assembly 81 and a cuff 96. Tether assembly 81 includes a tether 82 having a proximal end 84 and a distal end 86, and a tab 90 disposed at the distal end of the tether assembly. Tab 90 includes an aperture 92 extending therethrough. A plurality of bumps 88 may be provided along a surface of the tether. Non-linear lead-in portion 83 is provided along the length of tether 82, rather than at the proximal end as in the previous embodiment. In this embodiment, lead-in portion 83 is preferably provided near the midpoint of the length of tether 82, however it may optionally be provided at any point along the length of the tether.

As the tether is wound around cuff 96, lead-in portion 83 is initially threaded through aperture 92. Lead-in portion 83 may then be grasped at the opposite side of the aperture, and pulled in a manner such that tether 82 is folded, or "doubled-back", through aperture 92, as shown in FIG. 11. If desired, a suture 95 may be tied to join the free (proximal) end 84 of the tether to a point in the probe cable (electrical leads) 97, in a manner that allows a good deal of slack to remain in the cable (FIG. 11). With this embodiment, when it is desired to remove the probe, the physician pulls on cable 97, thereby exerting a force on suture 95 that in turn pulls tether 82 back through aperture 92. With the tether unlatched in this manner, the entire probe assembly (including cuff) can be removed from around the blood vessel and pulled out of the body.

Still another variation is shown in FIGS. 12 and 13. In this embodiment, assembly 100 includes a generally flexible tether 102 having a proximal end 104, a distal end 106, a lead-in portion 105, and a plurality of bumps 108 extending along a surface of the tether. Distal end 106 of tether 102 is affixed to tab 110 having aperture 112 therethrough. Cuff 114 is attached to the underside of tab 110. In this embodiment, bumps 108 are provided with a generally triangular profile, rather than the squared-off profile of bumps 18. When arranged as shown in FIG. 13, this configuration may provide a more secure "lock", thereby preventing tether 102 from recoiling back through aperture.

Figure 14:
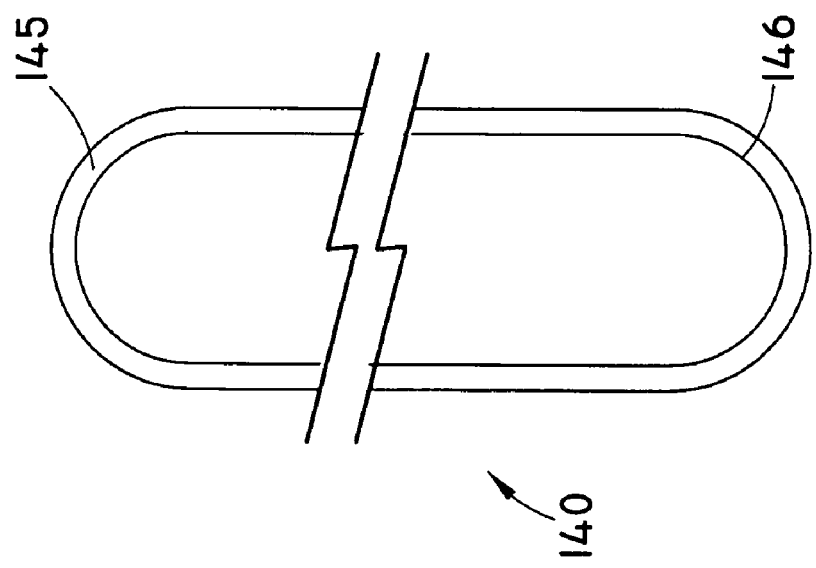
FIG. 14 illustrates an alternative configuration of a cuff design.
Figure 15:
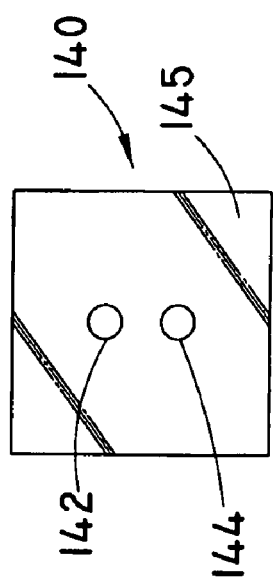
FIG. 15 illustrates a top view of the cuff design of FIG. 14, illustrating a relative position of the apertures.
Figure 16:
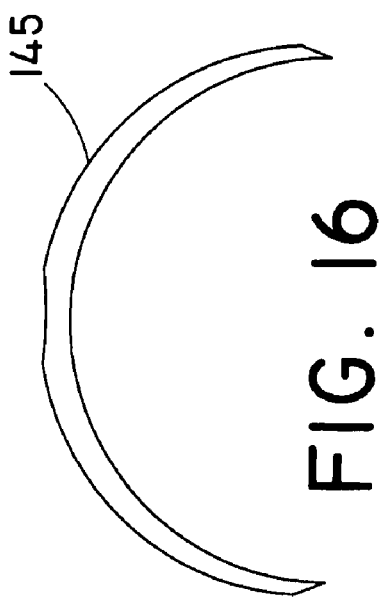
FIG. 16 illustrates a portion of the cuff of FIG. 14 that has been trimmed to a desired size.

Although the previous embodiments illustrate the cuff as having a generally circular configuration, this need not be the case. FIG. 14 illustrates a variation wherein a "universal" cuff 140 is provided. This cuff is sized and manipulatable such that it can accommodate vessels of varying sizes. In the embodiment shown, cuff 140 has a generally oval configuration similar to that of a racetrack. With this cuff, any excess cuff length may be simply trimmed off, so that the cuff can be sized to fit a particular vessel. Cuff 140 has a first end 145 and a second end 146. FIG. 15 illustrates aperture 142 for the tether, and another aperture 144 for the wires that extend from the transducer, extending through portions of cuff first end 145. The relative position of apertures 142, 144 is normally of little consequence along the surface of cuff 140, and the apertures may alternatively be positioned at other locations along the cuff. The unused end portion, in this case second end 146, may simply be trimmed away (FIG. 16) prior to installing the cuff onto the vessel, such that the cuff may be sized for precise fit around a particular vessel. This cuff may be used in conjunction with the assemblies described herein, or alternatively, as a stand-alone similar to a conventional cuff.

While these features have been disclosed in connection with the illustrated preferred embodiments, other embodiments of the invention will be apparent to those skilled in the art that come within the spirit of the invention as defined in the following claims.

What is claimed is:

1. A cuff assembly for placement around a body vessel, comprising:
   a cuff member sized to substantially surround said body vessel; and
   a tether assembly comprising a tether and a tab, said tab engaged with said cuff member and having an aperture therethrough, said tether having a proximal end and a distal end, said tether distal end engaged with said tab, said tether assembly sized for at least substantially encircling said cuff member, said tether assembly further including a locking mechanism for releasably maintaining a selected tension when said tether assembly encircles said cuff member, said locking mechanism comprising a plurality of stop members disposed along a surface of said tether, said stop members sized relative to said aperture to enable passage of at least a portion of said tether therethrough to encircle said cuff member when said stop members are aligned at a first angle relative to said aperture, and to substantially fix a position of said tether at a tension around said cuff member when said stop members are aligned at a second angle relative to said aperture.

2. The cuff assembly of claim 1, further comprising a lead-in portion along a length of said tether, said lead-in portion positioned for initial passage through said aperture.

3. The cuff assembly of claim 2, wherein said lead-in portion is configured for passage through said aperture and for hindering withdrawal in a reverse direction through said aperture.

4. The cuff assembly of claim 3, wherein said lead-in portion is substantially coil-shaped.

5. The cuff assembly of claim 1, further comprising an extension member juxtaposed between said cuff member and said tether assembly.

6. The cuff assembly of claim 5, wherein said extension member is collapsible into a contracted condition, further comprising at least one dissolvable suture member for maintaining said extension member in said contracted condition for a selected time period.

7. The cuff assembly of claim 1, wherein said stop members comprise a generally square-shaped profile.

8. The cuff assembly of claim 1, wherein said stop members comprise a generally triangular profile.

9. The cuff assembly of claim 1, further comprising a probe operationally engaged with said cuff member for providing a signal corresponding to a fluid flow in said body vessel.

10. A method for monitoring fluid flow in a body vessel, comprising:
    providing a cuff assembly, said cuff assembly comprising a cuff member sized to at least substantially encircle said body vessel, a probe member operationally engaged with said cuff member and alignable for providing a signal corresponding to fluid flow in said vessel, and a tether assembly engaged with said cuff member and sized for at least substantially surrounding said cuff member, said tether assembly having an aperture therein and a plurality of stop members disposed along a surface thereof and receivable through said aperture to a selected length for maintaining a selected tension when said tether assembly at least substantially surrounds said cuff member;

positioning said cuff assembly such that said cuff member substantially encircles said body vessel and said probe member is aligned for providing said signal;

wrapping a length of said tether assembly around at least a portion of said cuff member and threading a portion of said wrapped tether assembly including at least a portion of said stop members through said aperture to said selected length; and adjusting a position of said stop members relative to said aperture to substantially hinder withdrawal of threaded stop members back through said aperture.

11. The method of claim 10, wherein said tether assembly comprises a tether and a tab, said tab engaged with said cuff member and having said aperture therethrough, said tether having a proximal end and a distal end, said tether distal end engaged with said tab, and wherein said stop members are disposed along a surface of said tether.

12. The method of claim 11, wherein said stop members have at least one of a generally square-shaped profile and a generally triangular profile.

13. The method of claim 10, wherein said cuff member is trimmable to a selected length for at least substantially encircling said body vessel, said method further including the step of trimming said cuff member to said selected length prior to positioning said cuff assembly to at least substantially encircle said body vessel.

14. The method of claim 10, further comprising:

tying a first portion of a dissolvable suture to a proximal portion of said tether assembly, and a second portion of said suture to a distal portion of said tether assembly, in a manner such that a slack is formed along at least a portion of said tether assembly, said slack being at least substantially removed upon dissolution of said suture.

15. The method of claim 10, further comprising the step of trimming an excess length of said tether assembly threaded portion.

16. The method of claim 10, wherein said cuff assembly further comprises at least one elongated lead member communicating with said probe member for transmitting said signal to a processor.

17. An adjustable tension cuff assembly for positioning around a body vessel, comprising:

a cuff member sized to at least substantially encircle said body vessel;

a tab member engaged with a surface of said cuff member, said tab member having an aperture therethrough; and a generally flexible tether, said tether having a proximal end and a distal end, and a length sufficient to substantially surround said cuff member when said cuff member at least substantially encircles said body vessel, said tether distal end engaged with said tab member, a surface of said tether having a plurality of stop members disposed along at least a portion thereof, said stop members being sized and configured relative to said aperture to selectively enable passage of said tether and stop members through said aperture to at least substantially surround said cuff member and to substantially fix a position of said tether at a tension around said cuff member, and to selectively enable withdrawal of said stop members through said aperture to remove said tension.

18. The assembly of claim 17, wherein said stop members are sized and configured to substantially fix said position of said tether at said tension when said stop members are aligned at a first angle relative to said aperture, and to enable withdrawal through said aperture when aligned at a second angle relative to said aperture.

19. The assembly of claim 17, further comprising a probe member operationally engaged with said cuff member for providing a signal corresponding to a fluid flow in said body vessel.

* * * * *